United States Patent
Barnes

[11] Patent Number: 5,941,881
[45] Date of Patent: Aug. 24, 1999

[54] BONE FASTENING APPARATUS AND RELATED PROCEDURES

[75] Inventor: C. Lowry Barnes, Little Rock, Ark.

[73] Assignee: MedIdea, LLC, Ann Arbor, Mich.

[21] Appl. No.: 09/004,958

[22] Filed: Jan. 9, 1998

[51] Int. Cl.⁶ ................................. A61B 17/68
[52] U.S. Cl. .................. 606/71; 606/74; 606/207
[58] Field of Search .................. 606/69, 70, 71, 606/88, 61, 105, 72, 73, 74, 205, 206, 207, 208

[56] References Cited

U.S. PATENT DOCUMENTS

| | | | |
|---|---|---|---|
| 3,604,414 | 9/1971 | Borges | 606/105 |
| 3,659,595 | 5/1972 | Haboush | 606/71 |
| 3,824,995 | 7/1974 | Getscher et al. | |
| 4,120,298 | 10/1978 | Fixel | |
| 4,187,841 | 2/1980 | Knutson | 606/105 |
| 4,269,180 | 5/1981 | Dall et al. | |
| 4,473,068 | 9/1984 | Oh | |
| 4,565,192 | 1/1986 | Shapiro | 606/88 |
| 4,567,886 | 2/1986 | Peterson | 606/88 |
| 4,889,110 | 12/1989 | Galline et al. | |
| 4,957,496 | 9/1990 | Schmidt | 606/70 |
| 5,108,397 | 4/1992 | White | 606/60 |
| 5,324,291 | 6/1994 | Ries et al. | |
| 5,364,396 | 11/1994 | Robinson et al. | 606/53 |
| 5,415,658 | 5/1995 | Kilpela et al. | |
| 5,643,272 | 7/1997 | Haines et al. | 606/80 |
| 5,716,361 | 2/1998 | Masini | 606/86 |

Primary Examiner—Guy V. Tucker
Attorney, Agent, or Firm—Gifford, Krass, Groh, Sprinkle, Anderson & Citkowski, PC

[57] ABSTRACT

Apparatus and methods are disclosed to hold a bone piece in position relative to a host bone for attachment or re-attachment purposes. A body having a plurality of claws extending therefrom engages with the bone piece, at least one of the claws including a mechanism facilitating a first position wherein the claw is opened to fit onto the bone piece and a second position wherein the claw is actively urged into the bone piece. Depending upon the embodiment, the mechanism may include a claw-bearing member having one or more barbs, a claw-bearing member having teeth that engage with a gear, or a threaded post having a pointed end which is tightened through a portion of the body and locked into a desired position with the point actively urged into the bone. In yet a further embodiment of the invention, the claws of the device are pre-biased in a closed or gripping position, and a tool is used to temporarily spread the claws to fit over the bone piece, after which the tool is released, allowing the claws to dig into the surface of the bone.

5 Claims, 3 Drawing Sheets

BONE FASTENING APPARATUS AND RELATED PROCEDURES

FIELD OF THE INVENTION

This invention relates generally to instruments and surgical procedures used in the attachment and re-attachment of a bone pieces and, more particularly, to adjustable fasteners and methods of using the same to hold a bone section such as the greater trochanter in position during fusion.

BACKGROUND OF THE INVENTION

In many surgical procedures associated with proximal femoral reconstruction, osteotomy of the greater trochanter is often performed to expose the joint. Following the subsequent primary procedure, which may include partial or total hip replacement, it is important to reattach the trochanter with a stable force to ensure adequate long-term fusion and regrowth.

A popular device used for this purpose is known as the Dall-Miles cable, which refers to a system disclosed in U.S. Pat. No. 4,269,180, entitled BONE FASTENER FOR THE GREATER TROCHANTER. This and similar attachment systems are discussed elsewhere in the literature.

According to the Dall-Miles system, an H-shaped implant is used for reattachment of the greater trochanter following osteotomy, as shown in FIG. 1. The cross-bar of the H forms a bridge 12, and includes two through holes 14 to receive a cable 16, which is threaded through each hole in opposite directions.

To install the Dall-Miles system, a hole is drilled through the femur, preferably intersecting the medullary cavity. The cable is passed through the hole, and a surgical instrument is used to pull a loop of cable therethrough. The two ends of the cable are then fed in opposite directions as discussed above, then the crossbar of the H is crimped onto the cable to fix the implant in position. Prior to crimping, the cable is typically tensioned using conventional wire-tighteners, and after crimping, excess cable may be snipped off.

The upper and lower ends of the Dall-Miles device include claws 18, which are either impaled in, or bent to fit around the bone piece destined for re-attachment. Alternatively, the tips of the claws may be inserted into pre-drilled holes. Typically, however, the surgical practitioner uses a pliers or other instrument to bend the claws into the cortical outer layer of the trochanter, or around the edges of the bone piece, hoping to achieve a tight grip.

Thus one limitation of this system involves the haphazard way in which the claws of the implant engage with the outer surface of the bond to be reattached. In many instances, due to the irregular shape of the piece of bone requiring reattachment, it is difficult to predict how, and to what extent, the claws of the implant should be oriented to optimize engagement. The need remains, therefore, for apparatus and methods to attach such an implant to a bone in a more consistent manner. A more regimented approach should save time during surgery, while, at the same time, ensuring sufficiently rigid immobilization of a bone section to be reattached across the entire osteotomy site.

SUMMARY OF THE INVENTION

The present invention resides in devices, and methods of using the same, to hold a bone piece in position relative to a host bone for attachment or re-attachment purposes. Broadly, and in general terms, the invention includes a body having a plurality of claws extending therefrom to engage with the bone piece, at least one of the claws including a mechanism facilitating a first position wherein the claw is opened to fit onto the bone piece and a second position wherein the claw is actively urged into the bone piece. Means, such as cabling, are provided for holding the body with the bone piece attached thereto against the host bone until fusion takes place therebetween.

In one embodiment the mechanism includes a claw-bearing member having one or more barbs. The body is designed to receive the barbs, thereby locking the member into a desired position with the claw actively urged into the bone piece. In another configuration the mechanism includes a claw-bearing member having teeth, and the body includes a gear which engages with the teeth, enabling the member to be locked into a desired position with the claw actively urged into the bone piece by turning the gear. In a further embodiment the mechanism includes a threaded post having a pointed end which is tightened through a portion of the body and locked into a desired position with the point actively urged into the bone. In yet a further embodiment of the invention, the claws of the device are pre-biased in a closed or gripping position, and wherein a tool is used to temporarily spread the claws to fit over the bone piece, after which the tool is released, allowing the claws to dig into the surface of the bone.

DETAILED DESCRIPTION OF THE INVENTION

Figure 1:
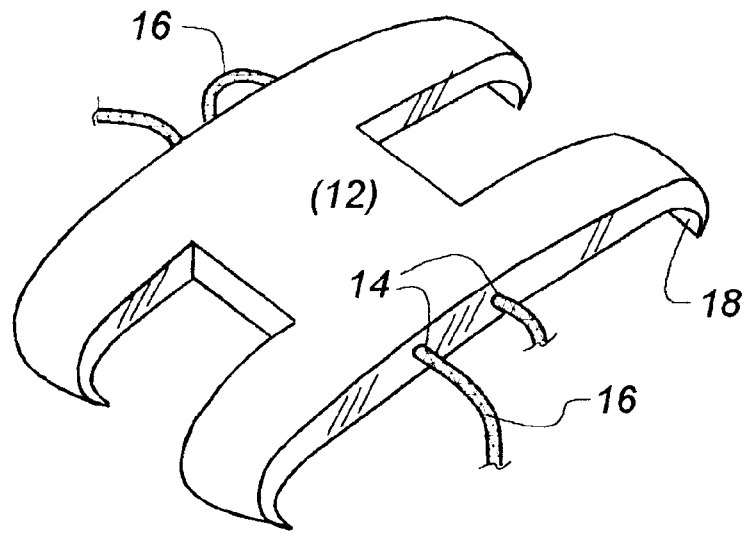
FIG. 1 is a drawing of a prior-art Dall-Miles bone fastener for use in re-attaching a greater trochanter.
Figure 2:
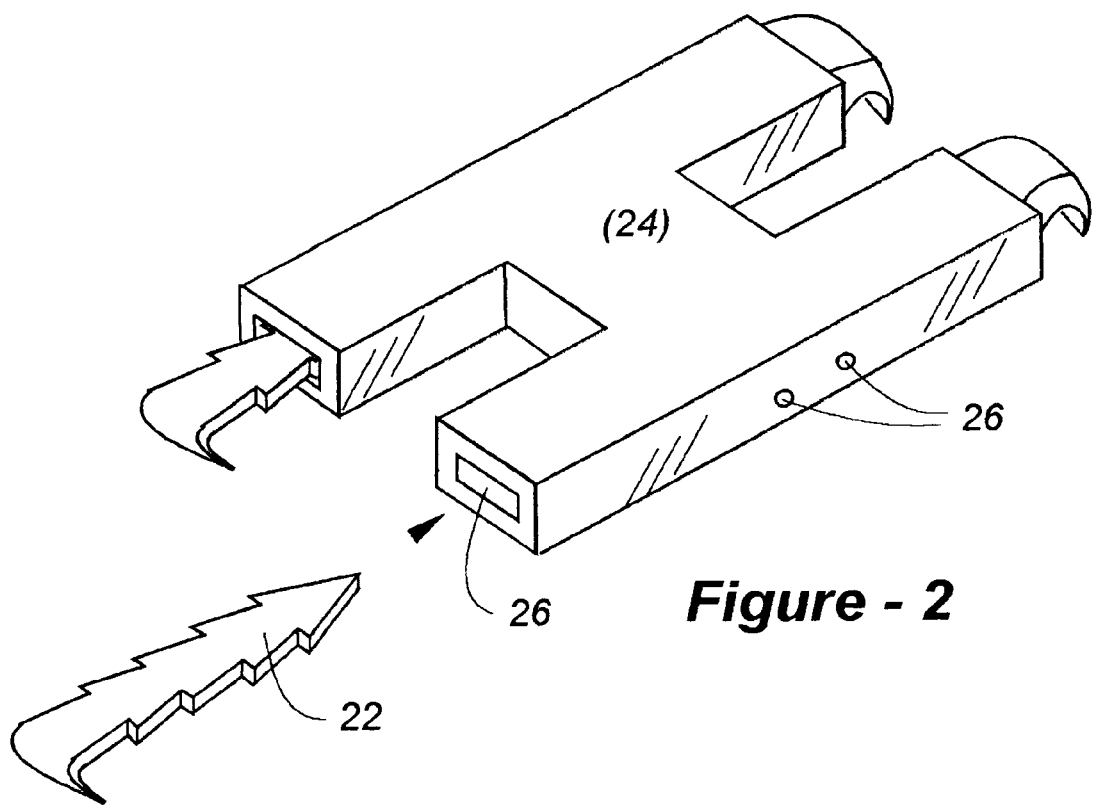
FIG. 2 illustrates one embodiment of the instant invention wherein a ratchet mechanism is used to clamp an implant onto a bone.

Now returning to the drawings, reference is made to FIG. 2, which illustrates one embodiment of the invention wherein one or more claw-bearing members 22 include barbs, and wherein the body 24 of the device includes an aperture into which the barbed portion is inserted and locked into position. Some or all of the claw-bearing members may include these barbs, depending upon the bone section to be attached or re-attached. For use with a greater trochanter, barbed claw members need only be provided on one side of the device, as shown in the Figure.

Each aperture 26 may include internal serrations, lips, or other features to better engage with the barbs such that, once ratcheted into place, the corresponding claw will not be able to back out, thereby resulting in a firm and consistent grasp. Similar to the Dall-Miles system, one or more transverse holes 26 are preferably included into which a cable may be introduced and crimped to lock the device onto the bone piece during fusion and regrowth. Means other than the Dall-Miles cable may also be provided, such as screws, reconstruction plates, and other types of clamps.

Figure 3:
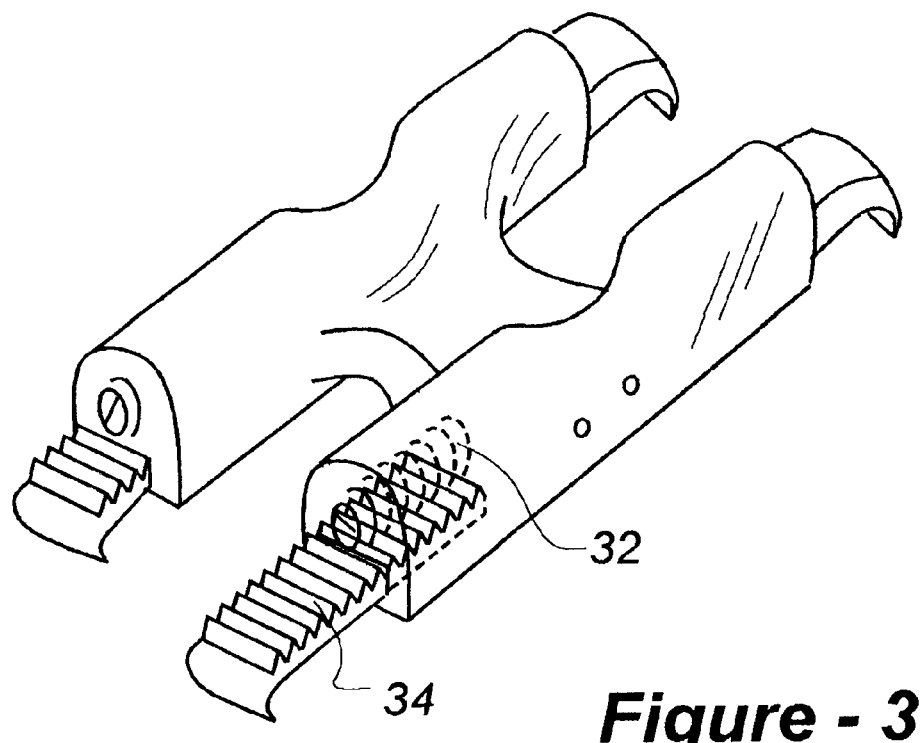
FIG. 3 is alternative embodiment of the invention where a worm gear is utilized in conjunction with a sliding claw member.

FIG. 3 illustrates an alterative embodiment of the invention wherein, instead of ratcheting pieces, a worm gear 32 is utilized along with claws having sections with teeth 34. By turning the worm gear with a screwdriver, allen wrench, or other appropriate tool, the gear rotates, pulling the claw with which it engages toward and into the bone piece to be secured. Again, one or more of the claws of the device may be provided with this capability and, indeed, a single worm gear having two sections of different handedness may be used with a pair of toothed claws, such that a single turning operation may be used to simultaneously bring both claws toward one another. Although the embodiment of FIG. 3 is somewhat more complex than that of FIG. 2, it does offer the advantage that the claws may be loosened to remove the clip, whether temporarily or permanently.

Figure 4:
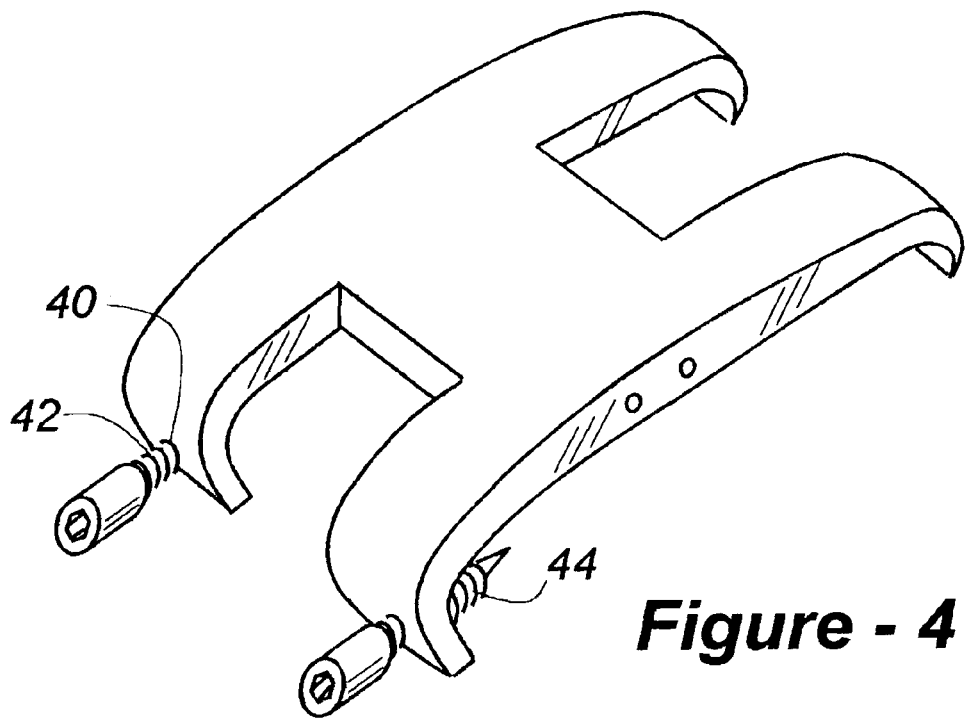
FIG. 4 illustrates a further alternative embodiment of the invention wherein a screw is used on one or both ends of an implant for clamping purposes according to the invention.

FIG. 4 illustrates yet a further embodiment of the invention wherein, instead of a ratchet mechanism or worm gear, a threaded hole 40 is provided into which a set screwtype element 42 is inserted, each element 42 including a pointed portion 44, which essentially forms the point of a claw in this configuration. A tool is used to turn the screw and move the move the point 44 toward, and into, the piece of bone to be secured, with the threads being chosen to minimize back out. Indeed, the threads between the hole and set screw may be slightly mismatched, causing resistance to tightening and resulting in a metal-metal interface much less conducive to loosening.

Figure 5:
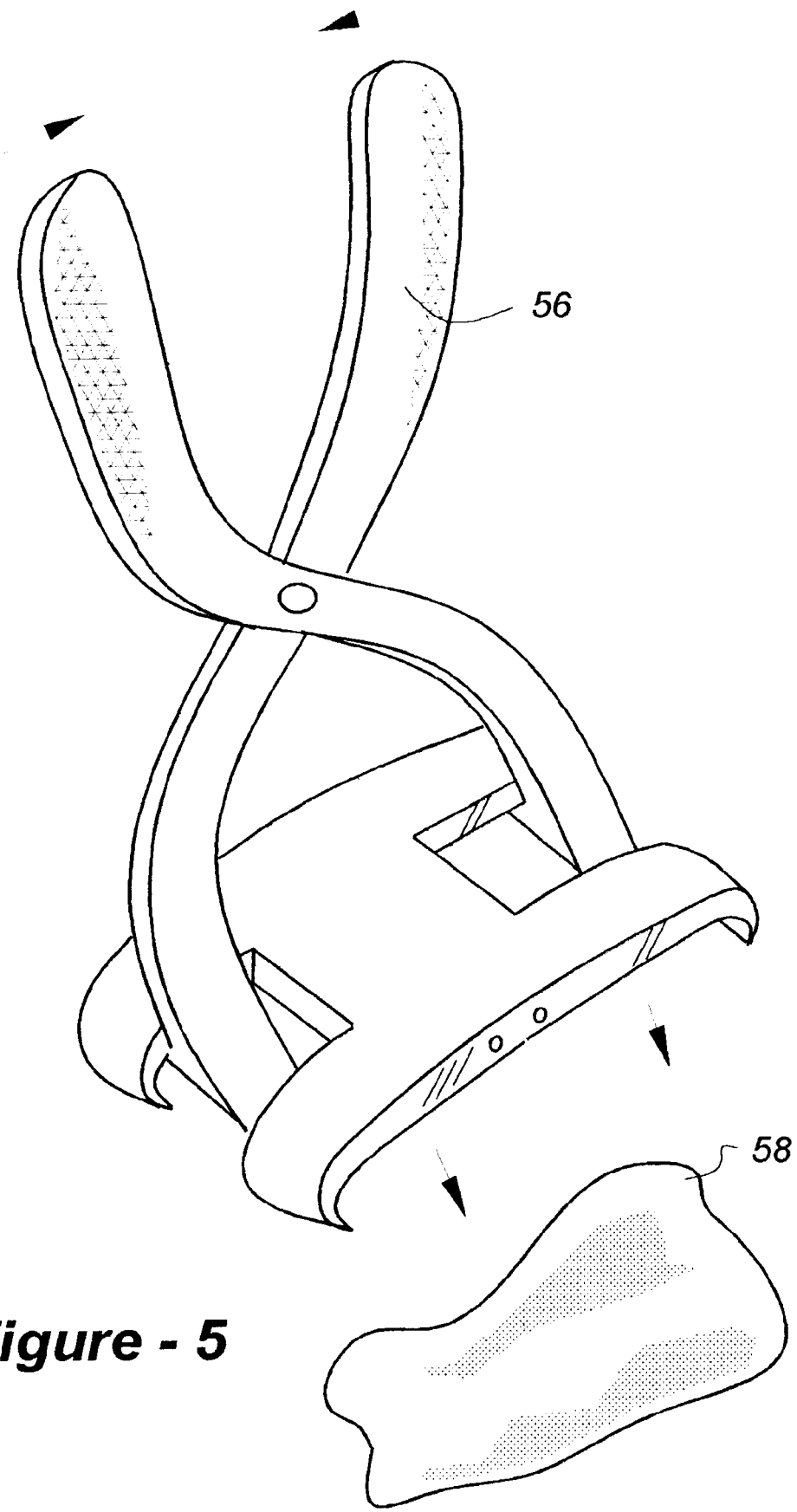
FIG. 5 depicts yet a further alternative embodiment of the invention wherein a spring clip is spread with a tool and released to grip a bone section.

FIG. 5 depicts yet a further alternative embodiment of the invention wherein the claws of the implant are pre-biased in a closed or gripping position, and a tool 56 is used to temporarily spread the claws to fit over a bone piece 58, after which the tool is released, allowing the claws to dig into the surface of the bone. Although the body of the device may include discrete springs for this purpose, in the preferred embodiment, the unit is at least partially constructed of a spring metal.

It will be apparent to one of ordinary skill that further variations are possible according to the invention, so long as one or more claws or tines of a bone clip may be actively moved into locking position with respect to a piece of bone to be grasped.

That claimed is:

1. A device to hold a bone piece in position relative to a host bone for attachment or re-attachment purposes, comprising:

a body including at least one pair of opposing claws extending therefrom, each claw terminating in a bone-engaging end section;

a mechanism facilitating a first position wherein the distance between the end sections is relieved to accommodate a bone piece to be retained, and a second position wherein the bone-engaging end sections are actively urged toward one another and against a bone piece; and cable retainer means for holding the body with a bone piece grasped thereby against a host bone to facilitate fusion therebetween.

2. The device of claim 1, wherein the mechanism includes a claw-bearing member having one or more barbs, and wherein the body receives the barbs, thereby locking the member into a desired position with the end sections actively urged against a bone piece to be retained.

3. The device of claim 1, wherein the mechanism includes a claw-bearing member having teeth, and wherein the body includes a gear which engages with the teeth, enabling the member to be locked into a desired position with the end sections actively urged against a bone piece to be retained by adjusting the gear.

4. The device of claim 1, wherein the mechanism includes a threaded post having a pointed end which is tightened through a portion of the body and locked into a desired position with the end sections actively urged against a bone to be retained.

5. The device of claim 1, wherein the claws of the device are pre-biased in an open or gripping position, and wherein a tool is used to temporarily spread or crimp the claws to fit over the bone piece, after which the tool is released, whereby the end sections dig into the surface of a bone piece to be retained.

* * * * *